United States Patent [19]

Kilbourn et al.

[11] 4,156,780
[45] May 29, 1979

[54] 3-PYRIDYLMETHYLTHIOCARBAMATES

[75] Inventors: Edward E. Kilbourn, Chalfont; Ernest D. Weiler, Ambler; William D. Weir, Levittown, all of Pa.

[73] Assignee: Rohm and Haas Company, Philadelphia, Pa.

[21] Appl. No.: 591,581

[22] Filed: Jun. 30, 1975

[51] Int. Cl.$^2$ ............................................. C07D 213/83
[52] U.S. Cl. ..................................... 546/330; 546/331; 546/12; 424/84
[58] Field of Search ..................... 260/295.5 C, 294.9, 260/294.8 F, 294.8 G; 424/84

[56] References Cited

U.S. PATENT DOCUMENTS

| 3,423,416 | 1/1969 | Hyatt | 260/294.8 E |
|---|---|---|---|
| 3,544,677 | 12/1970 | Lapham | 424/84 |
| 3,931,202 | 1/1976 | Ware et al. | 260/294.8 F |

OTHER PUBLICATIONS

Ware et al., Chem. Abstracts, vol. 80, (15), item No. 82,687t, Apr. 15, 1974.

*Primary Examiner*—Alan L. Rotman

[57] ABSTRACT

Novel 3-pyridylmethyl N-(4-substituted-phenyl)thiocarbamates are disclosed. These compounds are useful as single-dose rodenticides, which have high bait acceptance.

7 Claims, No Drawings

3-PYRIDYLMETHYLTHIOCARBAMATES

The present invention relates to 3-pyridylmethyl N-(4-substituted-phenyl)thiocarbamates and their acid organic and inorganic addition salts and metal salt complexes. These novel compounds are particularly useful, especially in compositions and formulations containing them, for the control and extermination of pest rodents.

The compounds of the present invention are depicted by the formula

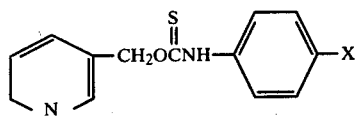  (I)

wherein X is cyano, methylcyano, nitro, mercapto, alkylthio, alkylsulfinyl, alkylsulfonyl, alkylsulfamyl and trihalomethyl, and the acid addition salts thereof.

Another embodiment of this invention is the metal salt complexes of the above compounds which have the formula:

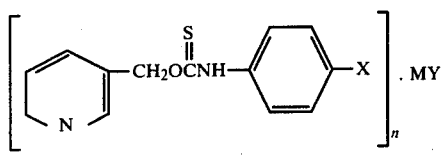  (II)

wherein X is as defined above and MY is a metal salt comprised of a cation such as calcium, copper, manganese, nickel, zinc and the like and an anion which satisfies the valence of the cation such as a bromide, chloride, nitrate, sulfate, oxalate and the like, which will form metal salt complexes with the 3-pyridylmethyl N-(4-substituted-phenyl)thiocarbamate.

The more preferred compounds of this invention are those wherein n is equal to one and X is cyano, nitro or methylthio and their acids addition salts and metal salt complexes. The most preferred embodiment of this invention is 3-pyridylmethyl N-(4-cyanophyenyl)thiocarbamate and its acid addition salts and metal salt complexes.

The term "alkyl" in the above description of the compounds of this invention is meant to designate an alkyl group of from 1 to 6 carbon atoms which may be straight chained or branched preferably a methyl group.

These compounds are readily prepared by the reaction of 3-pyridylcarbinol, a product of commerce, with an isothiocyanate. For best results the alcohol should be converted to its sodium derivative and preferably by the use of sodium hydride. The following equation depicts the reaction.

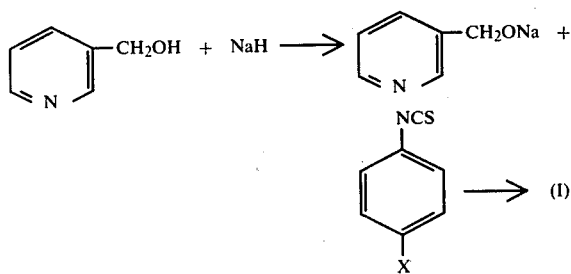

An inert solvent such as the monomethylether of ethylene glycol, diglyme, diethyl ether and the like can be used in this reaction. Generally, equimolar ratios of the reactants are used in this reaction, however, excesses of any of the reagents can be utilized. The reaction is usually carried out in the temperature range of about 0° to 50° C. and most often and preferably at room temperature.

Acid addition salt derivatives can be made by dissolving the pyridylmethylthiocarbamate in an appropriate solvent such as alcohol, acetone, methylethyl ketone and the like and adding to it an acid such as hydrochloric, hydrobromic, nitric, phosphoric, sulfuric, oxalic, citric, malic, tartaric and the like, either directly as a gas, liquid or solid; or as a solution wherein it is first dissolved in an appropriate solvent such as alcohol, acetone, methylethyl ketone and the like before adding it to the solution of the pyridylmethylthiocarbamate. The salt so obtained can be either collected on a filter directly or collected after the solvent is concentrated and then filtered or evaporated to dryness.

The metal salt complexes of this invention can be prepared by dissolving the pyridylmethylthiocarbamate in an appropriate solvent such as alcohol, acetone, methylethyl ketone and the like and adding to it a metal salt such as calcium, cupric, manganous, nickel and zinc bromides, chlorides, nitrates sulfates, oxalates and the like, either as a solid or as a solution wherein it is first dissolved in an appropriate solvent such as alcohol, acetone, methylethyl ketone and the like before adding it to the solution of the pyridylmethylthiocarbamate. The complex so obtained can be either collected on a filter directly or collected after the solvent is concentrated and then filtered or evaporated to dryness.

The following depicts the preparation of typical examples of the compounds of this invention. These examples are merely illustrations of the present invention and are not to be considered as limitations of the scope thereof.

EXAMPLE 1

Preparation of 3-pyridylmethyl N-(4-cyanophenyl)thiocarbamate

To a solution of 3-pyridylcarbinol (2.18g., 0.02 mole) in 50 ml. of glyme there is added sodium hydride (0.87g. of a 57% oil dispersion, 0.02 mole). The solution is allowed to stand 2 hrs. and then p-cyanophenyl isothiocyanate (3.2g., 0.02 mole) in 50 ml. of glyme is added dropwise. The reaction mixture is stirred at room temperature for 18 hrs. It is then saturated with sodium bicarbonate and poured into an excess of water. The resulting suspension is filtered to give a solid residue which is recrystallized from toluene to give 2.3g. of solid melting at 153°–154° C., with decomposition. The thiourea structure is confirmed by infra-red spectroscopy. The product is obtained in a 43.5% yield.

EXAMPLE 7

Preparation of 3-pyridylmethyl N-(4-cyanophenyl)thiocarbamate hydrochloride

The hydrochloride salt of Example 1 is made by dissolving 3-pyridylmethyl N-(4-cyanophenyl)thiocarbamate (1g., 0.0037 mole) in 75 ml. of acetone and passing in an excess of hydrogen chloride gas. A precipitate forms and is filtered, washed with acetone and dried to give 0.9g. of 3-pyridylmethyl N-(4-cyanophenyl)thiocarbamate hydrochloride melting at 198°–199° C., with decomposition.

EXAMPLE 8

Preparation of 3-pyridylmethyl N-(4-cyanophenyl)thiocarbamate zinc chloride complex The zinc chloride metal salt complex of Example I is made by dissolving 3-pyridylmethyl-N-(4-cyanophenyl)thiocarbamate (2.69g., 0.01 mole) in 75 ml. of methyl cellosolve and adding to this stirred solution; a solution of zinc chloride (0.68g., 0.005 mole) in 10 ml. of methyl cellosolve. The resulting solution is stirred at room temperature for 18 hours. The solvent is removed in vacuo and the residue is slurried in 30 ml. of methanol and collected on a filter to give 2.5g. melting at 174°–5° C. with decomposition.

EXAMPLE 9

Preparation of 3-pyridylmethyl N-(4-cyanophenyl)thiocarbamate oxalate

The oxalate salt of Example I is made by dissolving 3-pyridylmethyl-N-(4-cyanophenyl)thiocarbamate (2.69g., 0.01 mole) in 75 ml. of methyl cellosolve and adding to this stirred solution, a solution of oxalic acid dihydrate (1.26g., 0.01 mole) in 10 ml. of methyl cellosolve. The resulting thick suspension is allowed to stand at room temperature for 18 hours. The mixture is filtered and dried in vacuo to give 2.75g. melting at 189° C. with decomposition. The product structure is confirmed by infra-red spectroscopy.

The following Table I contains the physical characteristics of compounds prepared by the procedures given in Examples 1, 7, 8 and 9 above.

The following compounds can be prepared when the procedures as illustrated in Examples 1, 7, 8 and 9 are followed and the appropriate starting materials are utilized.

3-pyridylmethyl N-(4-mercaptophenyl)thiocarbamate
3-pyridylmethyl N-(4-methylsulfinylphenyl)thiocarbamate
3-pyridylmethyl N-(4-methylsulfonylphenyl)thiocarbamate
3-pyridylmethyl N-(4-isobutylthiophenyl)thiocarbamate
3-pyridylmethyl N-(4-hexylthiophenyl)thiocarbamate
3-pyridylmethyl N-(4-isopentylsulfonylpheny)thiocarbamate
3-pyridylmethyl N-(4-cyanomethylphenyl)thiocarbamate
3-pyridylmethyl N-(4-trifluoromethylphenyl)thiocarbamate
3-pyridylmethyl N-(4-isohexanoylphenyl)thiocarbamate
3-pyridylmethyl N-(4-nitrophenyl)thiocarbamate
3-pyridylmethyl N-(4-methylthiophenyl)thiocarbamate
3-pyridylmethyl N-(4-cyanoethylphenyl)thiocarbamate
3-pyridylmethyl N-(4-dimethylsulfamylphenyl)thiocarbamate
3-pyridylmethyl N-(4-acetylphenyl)thiocarbamate
3-pyridylmethyl N-(4-trichloromethylpheny)thiocarbamate
3-pyridylmethyl N-(4-hexylsulfinylphenyl)thiocarbamate
3-pyridylmethyl N-(4-butylsulfamylphenyl)thiocarbamate and the strong acid addition salts and metal salt complexes thereof.

TABLE I

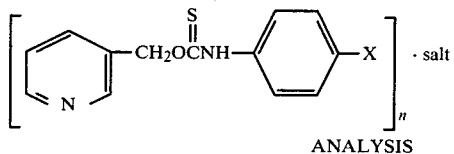

| Example No. | X | n | salt | Element | Calc'd. (%) | Found (%) | m.p.° C. |
|---|---|---|---|---|---|---|---|
| 1 | CN | 1 | — | C | 62.43 | 62.69 | 153–4 dec. |
|   |    |   |   | H | 4.12  | 4.19  |            |
|   |    |   |   | N | 15.60 | 15.55 |            |
| 2 | NO₂ | 1 | — | C | 53.97 | 53.64 | 166–7.5 |
|   |    |   |   | H | 3.83  | 3.67  |            |
|   |    |   |   | N | 14.52 | 14.23 |            |
| 3 | SCH₃ | 1 | — | C | 57.90 | 58.06 | 140–2 |
|   |    |   |   | H | 4.86  | 4.81  |            |
|   |    |   |   | N | 8.91  | 8.63  |            |
| 4 | C(O)C₃H₇-n | 1 | — | C | 64.94 | 64.93 | 119–21 |
|   |    |   |   | H | 5.77  | 5.76  |            |
|   |    |   |   | N | 8.91  | 8.63  |            |
| 5 | CF₃ | 1 | — | C | 53.84 | 53.73 | 131–3 |
|   |    |   |   | H | 3.55  | 3.57  |            |
|   |    |   |   | N | 8.97  | 9.02  |            |
| 6 | CH₂CN | 1 | — | C | 63.58 | 64.07 | 138–40 dec. |
|   |    |   |   | H | 4.62  | 4.51  |            |
|   |    |   |   | N | 14.83 | 14.33 |            |
| 7 | CN | 1 | HCl | C | 54.99 | 54.82 | 198–9 |
|   |    |   |   | H | 3.96  | 4.10  |            |
|   |    |   |   | N | 13.74 | 13.99 |            |
| 8 | CN | 1 | ½ (ZnCl₂) | C | 49.83 | 49.22 | 174–5 dec. |
|   |    |   |   | H | 3.27  | 3.57  |            |
|   |    |   |   | N | 12.45 | 11.85 |            |
|   |    |   |   | Zn | 9.69 | 8.80  |            |
| 9 | CN | 1 | oxalate | C | 53.47 | 52.92 | 189 dec |
|   |    |   |   | H | 3.65  | 3.97  |            |
|   |    |   |   | N | 11.69 | 11.39 |            |

Many compounds are toxic to rodents. However, very few of these compounds are suitable for use as rodenticides because it is necessary for the pest rodent to consume voluntarily a sufficient amount of the poison even though adequate supply of untreated food may also be available. In bait rodenticides safety and efficacy are highly important.

The 3-pyridylmethyl N-(4-substituted-phenyl)thiocarbamates and their salt derivatives of the present invention are highly toxic to a wide variety of pest rodents and a single dose is usually sufficient for control yet these compounds are relatively safe for use in the presence of the other species which may inadvertently ingest limited quantities of the rodenticide. Furthermore, rats and other pest rodents willingly consume the compounds in sufficiently lethal amounts when present in baits. Alternatively the compounds may be employed in compositions to be sprayed on natural foodstuffs. They may also be employed in a tracking powder, especially for use against mice, which habitually clean their paws by licking.

The compounds of the present invention may be formulated into rodenticide compositions such as baits, tracking powders, and sprays. A bait comprises an edible carrier and the toxicant optionally with a preservative to prevent insect infestation, mold growth or rancidity. The edible carrier may be a semi-moist material such as canned cat or dog food or garbage such as scraps of apples, eggs, bacon, etc., but it is generally preferred to use a dry edible carrier as this remains acceptable for longer periods. The dry carrier may be a combination of natural food products such as whole ground corn, steel cut oats, sugar, molasses, rice, vegetable oil, salt, dehydrated fruit, fish meal, tankage or wheat. When necessary to use in damp locations, the matrix may be a water repellent material such as paraffin wax or an acrylic polymer.

The compounds of the present invention may be incorporated as toxicant in bait formulations, either alone or in combination with other toxicants. When used as the sole toxicant in baits, the compounds of the present invention may be used in any rodenticidally effective concentration.

Depending on the susceptibility of the rodents to the toxicant and the amount of formulated bait generally consumed, concentrations as low as 0.1% and especially when intended for mice, even lower than 0.05% may be employed. A typical bait may contain between about 0.5% and 1.5% of the toxicant by weight. Example 10 describes the formulation of a suitable bait, although wide variations in formulation for different conditions of use are of course expected.

Tracking powders, which are particularly effective against mice may be either a compound of the present invention in finely powdered form or a mixture of the compound with powdered carrier, e.g., talc, sugar, milk powder, Indian corn meal, fish meal, cornstarch, flour, and bentonite, or the like, or any combination thereof which tends to induce the animals contaminated with the preparation to lick themselves more thoroughly. In tracking powders the compounds of the present invention may be incorporated in amounts from 100% down to 0.75% by weight, or somewhat less with proper formulation.

The thiocarbamates of this invention were preliminary evaluated for their ability to kill albino rats (*Rattus norvegicus*) by oral administration to two rats at a dosage of 50 mg./kg., and/or 200 mg./kg. In the standard test the effect on the rats is observed over a 14 day period.

The standard paired-preference test was used as a secondary test. In this test the rodents are given a free choice between the treated and untreated bait in individual cages. The cages were provided with dual feed cups and separate water devices. Such a test most nearly approximates practical use conditions.

The basal ration used for this test consisted of the following components all percentages being by weight:

EXAMPLE 10

Crude ground corn — 65%
Steel cut oats — 25%
Powdered sugar — 5%
Corn oil — 5%

A 3-pyridylmethyl N-(4-substituted-phenyl)thiocarbamate was blended with the basal ration in a Waring laboratory blender to form 50 grams of a homogeneous premix. The amount of compound utilized was determined by the percentage of active material desired in the feed. The 50 grams of premix containing the toxicant were then mixed with an additional 450 grams of basal ration. These components were mixed in a Little Ford Lodige mixer for three minutes. The basal ration was offered in excess of daily feed requirements in each of two feeders; one treated with the test compound and one without. For each test, equal numbers of each sex of albino rats were used.

The gross weight of each feed container and its feed were determined daily and returned to the starting weight by addition of complete replacement of the given diet. The position of the bait and the laboratory diet cups in the cage were reversed every 24 hours to counter any feeding position habit of the rat. The test rodents had free choice between treated and untreated feed. Mortalities were recorded daily.

The results of representative paired preferences tests with several dosage levels on individually caged rodents are given in Table II.

TABLE II

| Ex. No. | Rodenticidal Data | | | |
|---|---|---|---|---|
| | Oral Toxicity | | Paired-Preference Tests | |
| | Dosage (mg./kg.) | Mortality[a] | % Toxicant | Mortality[a] |
| 1 | 200 | 2/2 | 1% | 2/4 |
| | 50 | 1/2 | 2% | 4/4 |
| | | | 2%* | 2/4 |
| 2 | 200 | 2/2 | 1% | 1/2 |
| | 50 | 1/2 | 2% | 2/4 |
| 3 | 200 | 1/2 | 2% | 4/4 |
| | | | 2%* | 0/4 |
| 4 | 200 | 0/2 | 2% | 1/4 |
| 5 | 200 | 0/2 | 2% | 0/4 |
| 6 | 200 | 0/2 | 2% | 0/2 |
| 7 | 200 | 1/2 | 2% | 3/4 |
| 8 | 200 | 2/2 | 2% | 3/4 |
| 9 | | | 2% | 1/4 |

[a] albino rat
*Roof rat evaluation

The basal ration in which the toxicant of this invention can be incorporated can be selected from cereal grains such as corn, oats, wheat, rice, barley and the like and can include other excipients such as sugar, molasses, corn oil, peanut oil and the like. These ingredients can be made into a granular or a powdered formulation or gradients thereof.

The exact percentages of the ingredients that compose the basal ration can vary over a wide range covering anywhere from 0.01 to 99.9% by weight or volume.

However, a useful formulation of this invention consists of the following components, all percentages being by weight:

Finely ground corn — 43%
Steam rolled oats — 42.5%
Peanut oil — 5%
Powdered sugar — 5%
Finely ground molasses — 2.5%
Toxicant — 2%

The 3-pyridylmethyl N-(4-substituted-phenyl)thiocarbamate compounds, salts and metal salt complexes of this invention are useful rodenticides for controlling pest rodents. They can be formulated into both semi-dry bait preparation or into tracking powders. The scope of this invention is meant to include other methods for utilizing these compounds, salts and metal salt complexes that would suggest themselves to those skilled in the art of rodenticides.

We claim:

1. A compound of the formula

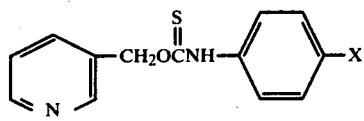

wherein X is cyano, nitro, mercapto, $(C_1-C_6)$ alkylthio, $(C_1-C_6)$ alkylsulfinyl, $(C_1-C_6)$ alkylsulfonyl or $(C_1-C_6)$ alkylsulfamyl; and the strong acid addition salts and metal salt complexes thereof.

2. A compound addition salt or metal salt complex according to claim 1 wherein X is cyano, nitro, methylthio, methylsulfinyl, methylsulfonyl, or methylsulfamyl.

3. A compound according to claim 2 wherein X is cyano.

4. A compound according to claim 2 wherein X is methylthio.

5. A compound according to claim 2 wherein X is nitro.

6. A salt according to claim 2 wherein the salt is a hydrochloride salt.

7. A salt according to claim 6 wherein X is cyano.

* * * * *